(12) United States Patent
Brabham et al.

(10) Patent No.: US 6,495,844 B1
(45) Date of Patent: Dec. 17, 2002

(54) METAL HALIDE LAMP FOR CURING ADHESIVES

(75) Inventors: Dale E. Brabham, Syracuse; Douglas M. Rutan, Auburn, both of NY (US); Timothy D. Russell, Westlake, OH (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 09/491,040

(22) Filed: Jan. 25, 2000

(51) Int. Cl.[7] .......................... H05B 41/00; H01J 61/20; G02B 5/28
(52) U.S. Cl. ..................... 250/504 R; 250/504
(58) Field of Search .................. 250/504 R, 504 H, 250/504; 313/638, 576

(56) References Cited

U.S. PATENT DOCUMENTS

| | | | | |
|---|---|---|---|---|
| 5,017,839 A | * | 5/1991 | Arlt et al. .................... 315/219 |
| 5,184,044 A | * | 2/1993 | Thomas ....................... 313/638 |
| 5,798,611 A | * | 8/1998 | Dolan et al. ................. 313/570 |
| 5,914,817 A | * | 6/1999 | Browning et al. ........... 359/634 |

* cited by examiner

*Primary Examiner*—John R. Lee
*Assistant Examiner*—Anthony Quash
(74) *Attorney, Agent, or Firm*—Wall Marjama & Bilinski LLP

(57) ABSTRACT

An arc lamp assembly which includes in combination a reflector and a light source which is surrounded by said reflector. A dichroic coating on the reflector functions to reflect radiation in the range of about 300 to 600 nm. The light source is an arc lamp which contains a metal halide fill component which includes a mixture of scandium iodide, or other suitable lanthanide, indium iodide, sodium iodide and sodium iodide, whereby the lamp assembly emits effective amounts of WV radiation to cure selected chemical compositions.

4 Claims, 3 Drawing Sheets

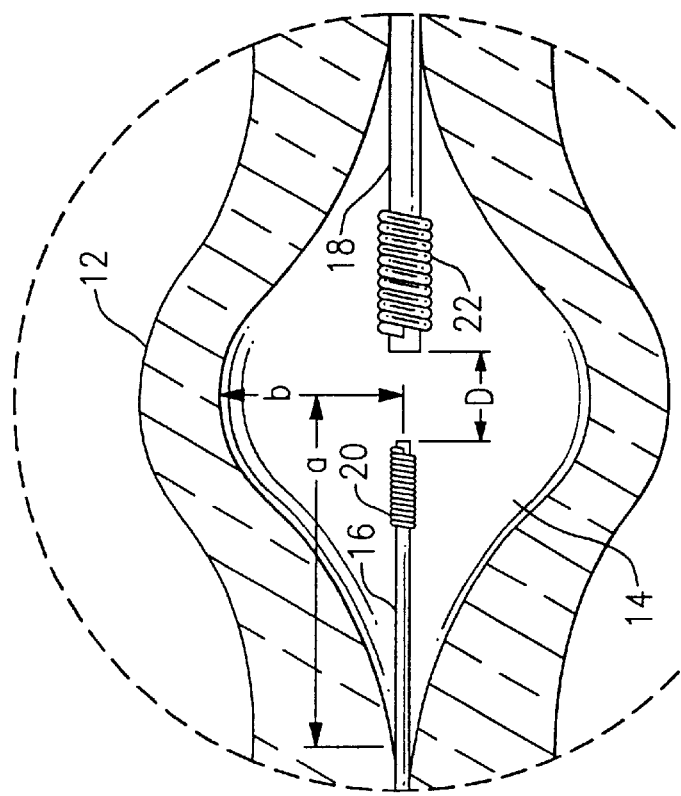
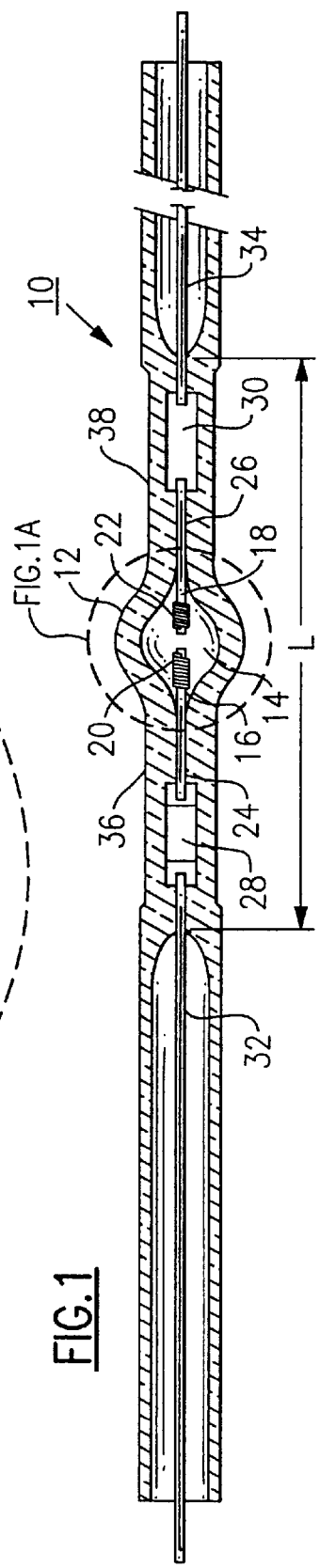
FIG.1A
FIG.1

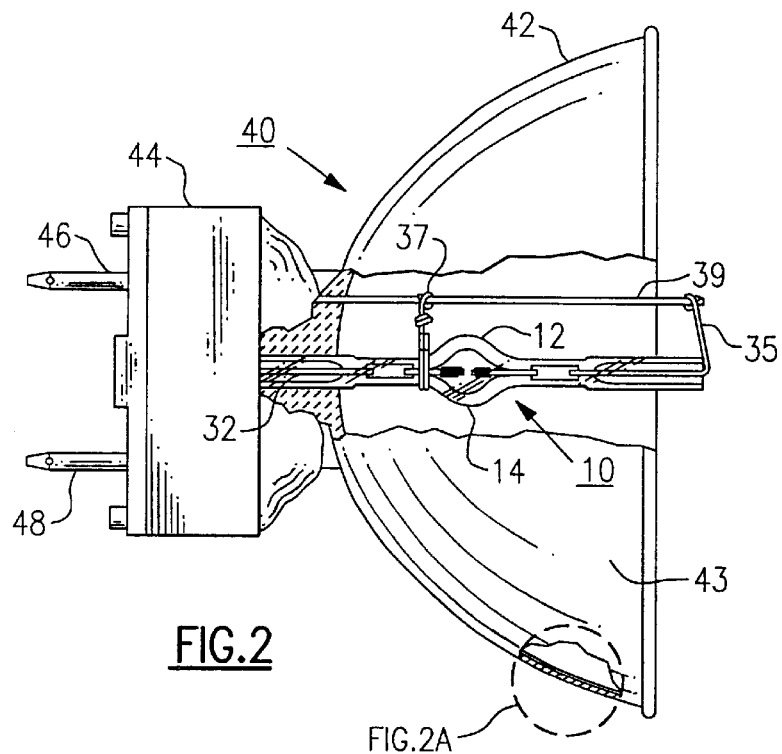
FIG.2
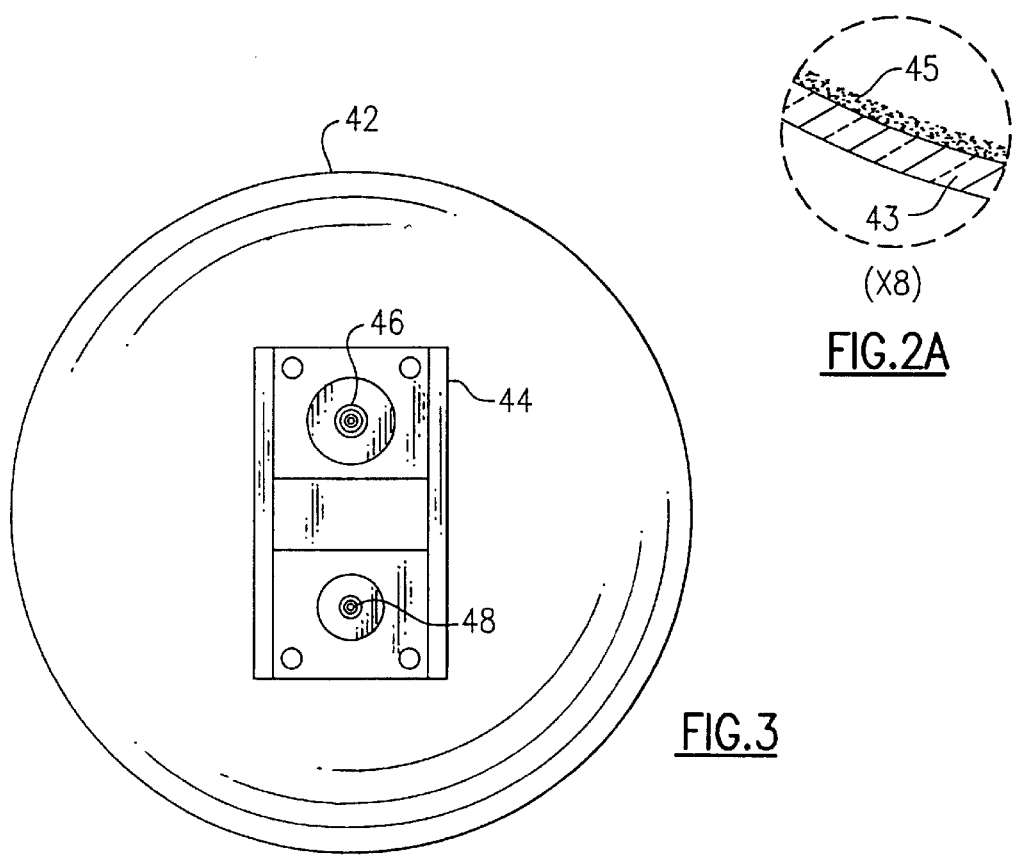
FIG.2A
FIG.3

METAL HALIDE LAMP FOR CURING ADHESIVES

BACKGROUND OF THE INVENTION

The present invention relates in general to lamps, and more specifically to a metal halide lamp which maximizes UV radiation in the desired useful range for curing chemical compositions.

It has long been a goal and objective in the field for a low wattage, long life, short arc gap lamp which could be used in a wide range of applications. Changing needs of the marketplace have identified the need for a short arc gap lamp in the range of 50 watts. Such an illumination source in one application could be used to irradiate small, light valves. This source would require a miniature source size, high radiance, good spectral properties, long life and low power. This goal was achieved with the development of a 50 watt arc lamp suitable for use as a projection lamp and is more fully described in U.S. Pat. No. 5,942,850.

When lamps of this type are attempted to be used in applications where UV radiation is required they are unsuitable in that even if operating conditions are modified to favorably promote UV radiation, lamp life or stability is compromised. Lamps of this type, therefore, do not satisfactorily operate to provide for enhanced radiation in the UV range, and as currently designed, are not candidates for applications where high UV response is essential.

It is therefore an object of the present invention to overcome the problems of the prior art described above.

It is a further object of the present invention to provide a high performance UV irradiation or light source which can be used as a curing light to initiate polymeric reactions in plastic and adhesive substrates.

It is a further object of the present invention to provide a high performance lamp for use in systems which require high UV radiation.

It is yet another object of the present invention to provide a compact lamp assembly which exhibits high radiance, long life, and good UV radiation.

SUMMARY OF THE INVENTION

The present invention is directed to a high performance miniature arc lamp. The lamp has a preferred use in curing chemical compositions which react to UV radiation. The lamp is used in an assembly that utilizes a dichroic coating on a reflector to concentrate UV light to the desired target or area.

It has been discovered that a unique metal halide mixture of individual compounds selected from the group of cesium iodide, indium iodide, scandium iodide, and sodium iodide provides a fill component which insures high lamp performance, and when used with a reflector having a suitable dichroic coating, is uniquely suited to providing an effective source of UV radiation.

A suitable mixture which accomplishes the objectives of the present invention comprises scandium iodide (or other suitable lanthanide), indium iodide, and alkali halides (sodium iodide and cesium iodide) in total amounts up to about 200 $\mu$g. The dichroic coating is selected to reflect UV radiation in a range from about 300 to 600 nm.

For use in the present invention it is essential that the lamp be of an acceptable miniature size, exhibit high radiance, long life and low power.

BRIEF DESCRIPTION OF THE DRAWING

For a fuller understanding of the nature and objects of the invention, reference should be made to the following detailed description of a preferred mode of practicing the invention, read in connection with the accompanying drawings, in which:

FIG. 1 is a side sectional view of the light source of the present invention.

FIG. 1a is an enlarged sectional view of the hermetically sealed chamber of the light source shown in FIG. 1.

FIG. 2 is a side sectional view of a lamp containing the light source of FIG. 1.

FIG. 2A is an enlarged sectional view taken through the sidewall of the reflector shown in FIG. 2.

FIG. 3 is a rear view of the lamp shown in FIG. 1.

DETAILED DESCRIPTION OF THE INVENTION

Figure 4:
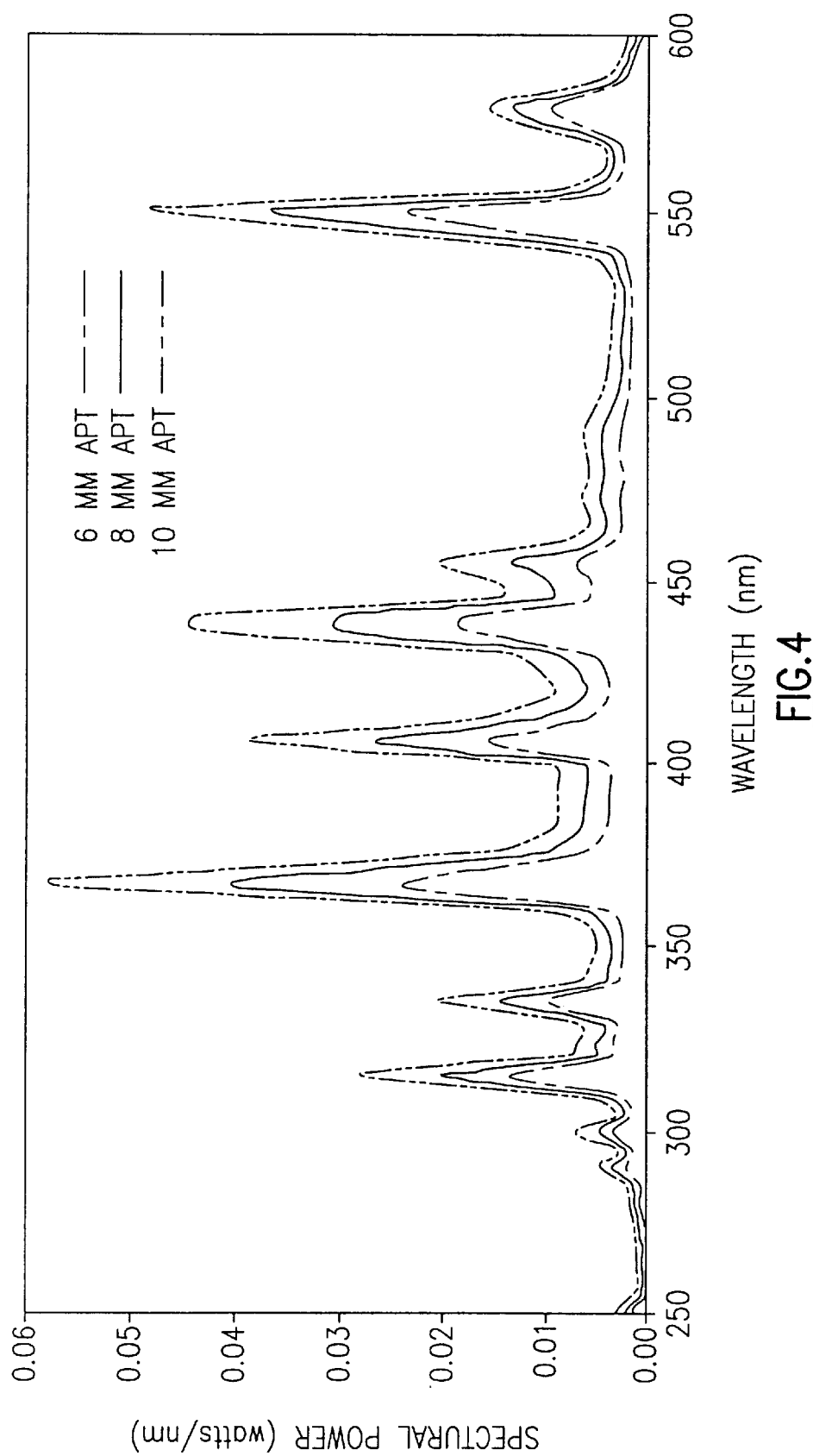
FIG. 4 illustrates a plot of the UV output of the lamp of the present invention at three different apertures.

The light source 10 of the present invention in the form of an elongated fused quartz envelope is shown in more detail in FIG. 1 as being a double ended structure having a pair of elongated electrodes 16 (cathode) and 18 (anode) disposed at opposite ends of neck sections 36 and 38, respectively. The electrodes are separated from each other by a predetermined critical distance D or arc gap preferably in the range of about 0.8 mm to about 1.5 mm. The light source is in the shape of an elongated body having an overall length (L in FIG. 1) in the range of about 28 mm to about 32 mm having the neck sections with a diameter in the range of about 3 mm to about 5 mm, and has a generally ellipsoidal shaped central hermetically sealed chamber 2 having a volume 14 of about 130 mm$^3$±20 mm$^3$. The wall thickness of chamber 2 s about 1 mm. The light source contains a critical fill mix which comprises an inert noble gas, mercury and metal halides which are formulated to enhance, UV output.

More specifically, the sealed chamber is designed to provide a unique UV spectral response for the lamp of the present invention as evidenced by the plot of spectral power in the UV range of about 300–600 nm as shown in FIG. 4. The radiation illustrated in FIG. 4 is obtained from the lamp described herein operated at 50 W with a spectroradiometer traceable to NIST standards.

The volume of the chamber can be approximated to that of an ellipsoid of semi-major axis a and semi-minor axis b.

$$V = 4/3 \pi b^2 \cdot a$$

The semi-major axis length (a in FIG. 1a) for the light source of the present invention is one half of the overall chamber length and in a range of about 4 to 6 mm. The semi-minor axis length (b in FIG. 1a) is one half of the chamber inner diameter and has a range of about 2 to 3 mm.

The preferred range of the chamber volume to yield optimal performance specifications is about 110 to 150 mm$^3$. The lamp power divided by the chamber volume is known as the volume-power loading of the lamp. This number calculates out to be 0.4/mm$^3$ given the preferred range of design factors. This metric is significant because it relates to the amount of heat dissipated power unit size of the lamp and therefore influences the operating temperature of the lamp.

The appropriate volume of the chamber is determined in combination with other interrelated design factors, primarily the type and amount of fill materials and operating power.

Deviation from the optimal volume could lead to performance degradation as a result of either improper internal operating pressure or improper thermal operation as dictated by the volume-power loading.

The electrodes respectively consist of a shank portion the ends of which contain wrapped metal coils 20 and 22, respectively. Proper thermal and electrical design of electrodes are required to achieve the desired performance. Coils, or wraps of wire, around the primary electrode shank can be added to properly balance the electrical and thermal requirements. Coils can serve the function of providing an additional thermal radiative surface to control the temperature of the electrode shank. The size and length of the coil can be designed to achieve optimal thermal performance. An additional function of coils is to provide the appropriate electrical field properties for efficient and reliable arc initiation, or lamp starting. In certain applications, the coil on the cathode is optional and is not required. The opposite end of the shank portions are respectively connected to one end of a foil member 28 and 30 respectively sealed in the opposite end of the neck portion. Typically, the foil members are made of molybdenum. The foil members have their other end respectively connected to relatively thicker outer lead wires 32 and 34 which in turn are respectively connected to the structural members shown more clearly in FIG. 2.

FIG. 2 illustrates the miniature lamp 40 of the present invention which includes a reflector 42 containing the light source 10 having an insulating thermally resistant connector 44 having a pair of pins 46 and 48 suitable for connection to a suitable source of power. Structural members 35, 37 and 39 are used to orient the light source in a substantial horizontal axis with respect to the reflector and form the electrical connections along with lead wire 32. The reflector internal glass surface 43 further contains a coating of dichroic material 45 which function to transmit selected light, and reflect or direct UV radiation to a desired target or location. Suitable dichroic materials are combinations of silicon dioxide ($S_1O_2$), aluminum oxide ($Al_2O_3$), zirconium dioxide ($ZrO_2$), or tantalum oxide ($Ta_2O_5$). Multiple coatings are applied in alternating layers. The dichroic coating is a submicron layer, typically about 0.005 to 0.010 microns thick. Multiple coatings (up to 100) of at least two different oxides are alternately formed on the inside surface of the reflector by a conventional vapor deposition technique.

In the present invention, a refractory insulating material is formed into an elongated envelope into which the following components are inserted and hermetically sealed:

a. a pair of refractory metal electrodes;

b. a quantity of metal halide material;

c. a quantity of metallic mercury; and d. a quantity of an inert noble gas.

The electrodes are aligned in an axial manner facing each other. The light source is operating in a direct current (DC) mode at a low electrical power.

Refractory materials for the envelope can be fused silica or alumina oxide. The refractory materials for the electrodes typically are tungsten (with or without thorium) or molybdenum. The description of electrodes is defined in more detail below. The metal halide materials and quantity of mercury is also described below.

Preferably the envelope material is fused silica and the electrodes are tungsten. Fused silica is easier to handle and process, and tungsten allows for higher operating temperatures and increases light output and life.

The opposing electrodes are set apart and separated at a distance to provide optimal performances for projection display applications Maximum utilization of optical component light collection requires the light source to be as near to "point source" as possible.

The broad range of separation is 0.8 mm to 1.5 mm.

The preferred range of separation is 1.2 mm±0.2 mm.

Falling below the preferred range of separation will cause a corresponding loss in lamp luminous efficacy. Exceeding the preferred range will minimize the effectiveness of the lamp as a miniature source for projection optics.

In operating the light source in a DC mode, one electrode is identified as the anode, the other as the cathode, and each is sized appropriately for optimal operation for a given lamp power and current. The electrodes are constructed from known techniques that incorporate an overwound refractory metal coil attached to the metal shank. The optimal design is determined given the range of electrical power and current over which the source is intended to operate. The table below tabulates the electrode wire diameters and power and current ranges for the present invention.

|  | Range of Wattage: 40 W–60 W Range of Current: 0.5 A–1.5 A | Preferred Wattage: 50 W ± 2 W Preferred Current: 0.9 A ± .2 A |
|---|---|---|
| Anode Shank | 0.020 in. ± 0.008 in. | 0.020 in. ± 0.001 in. |
| Anode Overwind Wire | 0.010 in. ± 0.005 in. | 0.010 in. ± 0.001 in. |
| Cathode Shank | 0.014 in. ± 0.004 in. | 0.014 in. ± 0.001 in. |
| Cathode Overwind Wire | 0.005 in. ± 0.005 in. | 0.007 in. ± 0.001 in. |

A mismatch between electrical operating characteristics and electrode design could be disastrous from a product performance standpoint. Generally, a design that permits too high of an operating temperature of the electrodes (high current/small electrodes) will result in rapid electrode erosion, darkening of the envelope, short life and low light output. Too low of an operating temperature of the electrode (low power/large electrodes) will result in an unstable or flickering arc.

In has been discovered that a unique metal halide mixture of individual compounds selected from the following group of scandium iodide, indium iodide, cesium iodide, and sodium iodide in conjunction with the other fill components results in a lamp which exhibits enhanced UV output. It is the specific dose of metal halide salts in combination with a reflector having a dichroic coating that concentrates only the desired UV radiation that is the key combination of components of the present invention.

The scandium iodide, or any other suitable lanthanide, provides a means of controlling undesired secondary processes within the lamp. The indium iodide contributes radiation emission in the blue to ultraviolet regions to enhance the total spectral output fundamental to this invention. The sodium iodides and cesium iodides are introduced in combination to provide the appropriate electrical, thermal, and convective characteristics of the plasma.

A suitable mixture, shown in the table below, which accomplishes the objectives of the present invention is a metal halide dose of 132 μg of material composed of (by mass percent). The operative concentration range which provides a combination that optimize stable electrical behavior is also listed in the table below:

| Compound | Mass Percent (Wt. %) | Operative Range |
|---|---|---|
| $ScI_3$ | 10.9 | 5–25 μg |
| InI | 5.0 | 3–15 μg |
| NaI | 79.1 | 10–200 μg |
| CsI | 5.0 | 10–200 μg |

The quantity of mercury is added such that it will evaporate and enter the discharge in a gaseous state and regulate the electrical operational parameters.

The amount of mercury can range from 5 to 15 milligrams and is a function of the internal volume of the envelope.

The preferred amount being about 9 milligrams ±–10%.

Excess mercury will cause excess pressure within the bulb and could result in early failure. Too low of an amount of Hg could result in improper electrical operating characteristics, primarily thereby reducing luminous efficacy.

The fill inert gas is added to provide a gas that can be ionized to aid in the starting of the lamp. Suitable fill gasses include Ne, Ar, Kr, and Xe with cold fill pressures in the range of 0.5 atm to several atmospheres.

A preferred gas for use in the present invention is Ar at about 500 Torr±2%. Excess Ar would cause the required voltage to initiate the discharge to be very high and impose large costs on the electrical operating circuitry.

The above specification for the electrode arc gap, quantity of metal halide, mercury, and noble gas must be used in conjunction with an hermetically sealed chamber having a critical volume, which in the case of the present invention is about 130 mm$^3$±20 mm$^3$.

The source size is dictated by the electrode separation (arc gap) in the range of 0.8 mm to 1.5 mm. The overall length of the envelope and associated structure being about 2 inches long. The service life exceeding 2,000 hrs.

The light source and lamp of the present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. An arc lamp assembly which provides an effective source of UV radiation for curing chemical compositions, which includes in combination a reflector and a light source which is surrounded by said reflector, the improvement comprising a dichroic coating on said reflector which functions to reflect radiation in the range of about 300 to 600 nm, and where said light source is an arc lamp which contains a metal halide fill component which includes a mixture of scandium iodide, indium iodide, portions of cesium iodide and sodium iodide, and where said metal halide mixture has the following concentrations: ScI$_3$ in the range of 5–25 μg, InI in the range of 3–15 μg, NaI in the range of 10–200 μg, and CsI in the range of 10–200 μg.

2. A miniature lamp which provides an effective source of UV radiation for curing chemical compositions which includes a reflector which surrounds a light source wherein
   (a) said reflector contains a dichroic coating selected to reflect UV radiation in the range of about 300 to 600 nm; and
   (b) said light source including an elongated fused quartz envelope having a pair of opposite neck portions each with a coaxial central opening having a reduced section and a central hermetically sealed chamber containing a fill comprising;
   an argon pressure at room temperature at a range of about 0.5 atmospheres to about 2.0 atmospheres; mercury in an amount in the range of about 5 mg to about 15 mg; a mixture of metal halide material in an amount from about 50 up to 1000 micrograms wherein said metal halide mixture comprises scandium iodide, indium iodide, cesium iodide and sodium iodide, a pair of axially aligned electrodes respectively positioned at said opposite neck portions and separated from each other by a predetermined distance from about 0.8 to 1.5 mm, said electrodes each having a shank portion which includes a distal end, with at least one of said ends having a coil wrapped around said end.

3. The lamp of claim 2 in which the metal halide mixture comprises the following concentrations: ScI$_3$ in the range of 5–25 μg, InI in the range of 3–15 μg, NaI in the range of 10–200 μg, and CsI in the range of 10–200 μg.

4. The lamp of claim 2 in which the dichroic coating is a material selected from the group consisting of silicon dioxide, aluminum oxide, zirconium dioxide, tantalum oxide in a plurality of alternating layers of different oxides.

* * * * *